United States Patent
Gregory et al.

(10) Patent No.: US 9,759,699 B1
(45) Date of Patent: Sep. 12, 2017

(54) SYSTEMS AND METHODS FOR THE DETECTION OF COMPOUNDS

(71) Applicant: Rhode Island Board of Education, State of Rhode Island & Providence Plantations, Providence, RI (US)

(72) Inventors: Otto J. Gregory, Wakefield, RI (US); Daniel Mallin, Cranston, RI (US); Zach Caron, Hope, RI (US); Mitch Champlin, Narraganset, RI (US)

(73) Assignee: Council on Postsecondary Education, Warwick, RI (US)

( * ) Notice: Subject to any disclaimer, the term of this patent is extended or adjusted under 35 U.S.C. 154(b) by 97 days.

(21) Appl. No.: 14/719,400

(22) Filed: May 22, 2015

(51) Int. Cl.
  G01N 7/00 (2006.01)
  G01N 33/00 (2006.01)
  G01N 33/22 (2006.01)

(52) U.S. Cl.
  CPC ....... G01N 33/0013 (2013.01); G01N 33/227 (2013.01)

(58) Field of Classification Search
  CPC ............ G01N 33/4972; G01N 33/497; G01N 1/2273; G01N 1/24; G01N 33/0011; G01N 2001/2223; G01N 1/2214; G01N 1/2226; G01N 27/4077; G01N 27/12; G01N 27/407; G01N 21/783; G01N 27/126; G01N 2030/025; G01N 27/4162; G01N 33/0013; G01N 33/227; G01N 33/22; A61B 5/097
  USPC ............. 73/23.3, 31.01, 31.02, 31.03, 31.05, 73/31.07; 422/83, 90
  See application file for complete search history.

(56) References Cited

U.S. PATENT DOCUMENTS

| | | | | |
|---|---|---|---|---|
| 5,137,924 A * | 8/1992 | Short | ...................... | B01J 23/63 518/700 |
| 5,731,510 A * | 3/1998 | Jones | ................... | G01N 29/022 73/114.71 |
| 5,997,832 A * | 12/1999 | Lieber | .................... | B82Y 30/00 423/249 |
| 6,171,378 B1 * | 1/2001 | Manginell | .............. | G01N 30/12 55/DIG. 5 |
| 7,147,695 B2 * | 12/2006 | Mitra | ..................... | G01N 30/12 204/192.1 |
| 7,329,389 B2 * | 2/2008 | Horovitz | .............. | G01N 27/123 29/592 |
| 7,581,434 B1 * | 9/2009 | Discenzo | ........... | G01N 33/2888 73/53.01 |
| 7,972,863 B2 * | 7/2011 | Trygstad | .............. | G01N 21/359 356/3 |
| 2001/0003249 A1 * | 6/2001 | Stormbom | ........... | G01N 27/223 73/1.06 |

(Continued)

OTHER PUBLICATIONS

Diaz Aguilar, A., et al. "A hybrid nanosensor for TNT vapor detection." Nano letters, vol. 10, Issue 2 (2009), pp. 380-384.

(Continued)

*Primary Examiner* — John Fitzgerald
*Assistant Examiner* — Truong D Phan
(74) *Attorney, Agent, or Firm* — Gesmer Updegrove LLP

(57) ABSTRACT

A gas sensor system is disclosed for detection of a compound that decomposes upon exposure to a metal oxide catalyst. The gas sensor system includes a sensor which includes a microheater, and a metal oxide catalyst that covers the microheater. The gas sensor system includes a pre-concentrator upstream from the sensor that lowers the limit of the detection of a compound.

20 Claims, 14 Drawing Sheets

(56) References Cited

U.S. PATENT DOCUMENTS

| | | | | |
|---|---|---|---|---|
| 2004/0241870 | A1* | 12/2004 | Miller | G01N 27/16 436/151 |
| 2005/0011260 | A1* | 1/2005 | Arndt | G01P 15/18 73/204.26 |
| 2005/0109621 | A1* | 5/2005 | Hauser | G01N 27/44791 204/451 |
| 2005/0260453 | A1* | 11/2005 | Jiao | B82Y 30/00 428/698 |
| 2006/0254501 | A1* | 11/2006 | Wang | B82Y 10/00 117/68 |
| 2007/0105341 | A1* | 5/2007 | Sosnowchik | B23K 1/0016 438/455 |
| 2008/0093226 | A1* | 4/2008 | Briman | G01N 27/127 205/775 |
| 2008/0148815 | A1* | 6/2008 | Lucas | G01N 30/08 73/23.41 |
| 2009/0218235 | A1* | 9/2009 | McDonald | G01N 27/127 205/775 |
| 2009/0235862 | A1* | 9/2009 | Cha | C30B 25/00 117/94 |
| 2009/0249859 | A1* | 10/2009 | Takahashi | G01N 27/16 73/23.31 |
| 2010/0213603 | A1* | 8/2010 | Smeys | H01L 21/4853 257/698 |
| 2011/0128828 | A1* | 6/2011 | Naniwa | G11B 5/3133 369/13.23 |
| 2011/0149465 | A1* | 6/2011 | Hashimoto | H01G 11/12 361/301.4 |
| 2012/0041246 | A1* | 2/2012 | Scher | B01J 21/066 585/500 |
| 2012/0192623 | A1* | 8/2012 | Adami | G01N 33/007 73/31.05 |
| 2012/0301360 | A1* | 11/2012 | Meinhold | B01J 20/28047 422/68.1 |
| 2014/0036953 | A1* | 2/2014 | Kimura | G01J 5/16 374/121 |
| 2014/0212979 | A1* | 7/2014 | Burgi | G01N 33/0016 436/34 |
| 2015/0316523 | A1* | 11/2015 | Patolsky | G01N 27/4146 506/2 |

OTHER PUBLICATIONS

Sysoev, V. V., et al. "Percolating SnO 2 nanowire network as a stable gas sensor: Direct comparison of long-term performance versus SnO 2 nanoparticle films." Sensors and Actuators B: Chemical vol. 139, Issue 2 (2009), pp. 699-703.

* cited by examiner

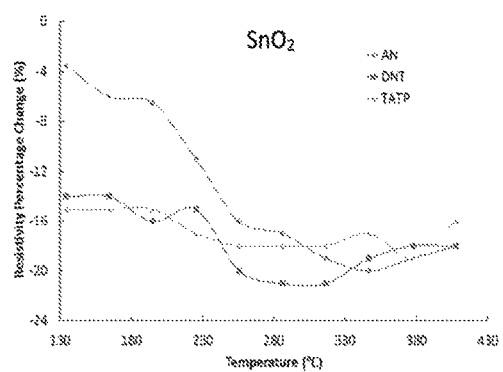
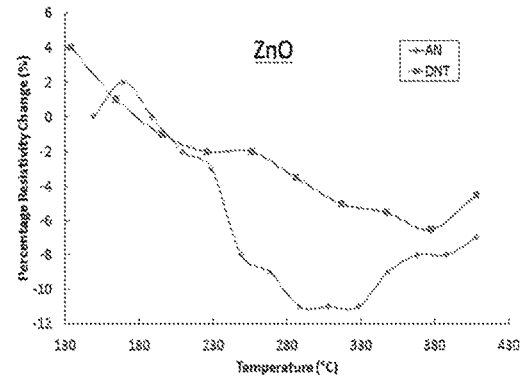
FIG. 6A              FIG. 6B
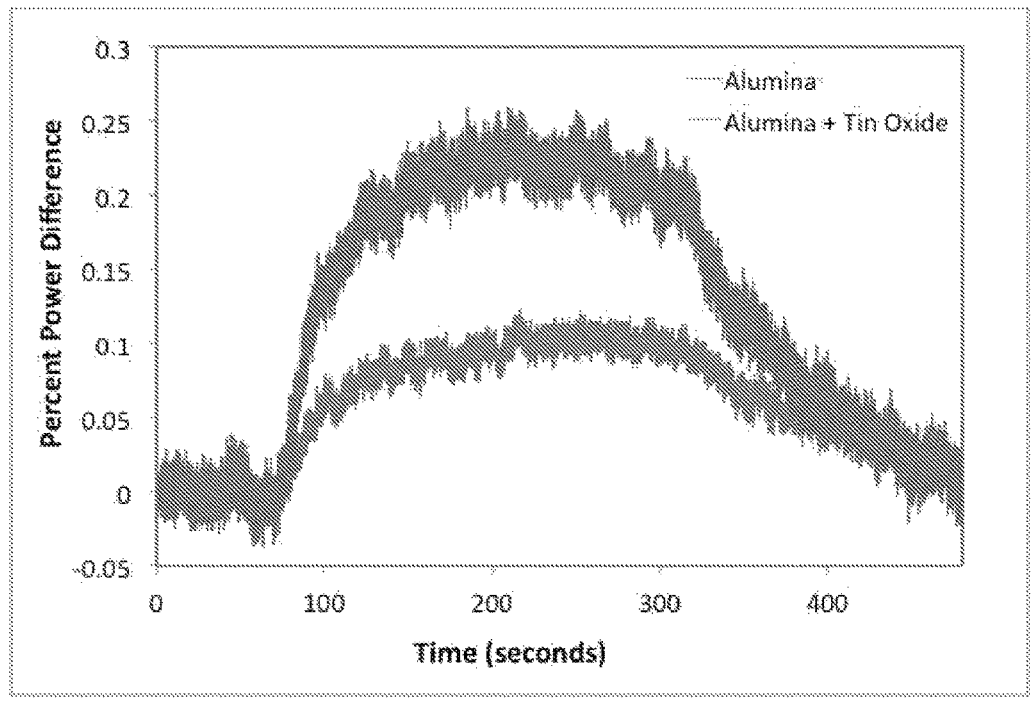
FIG. 7

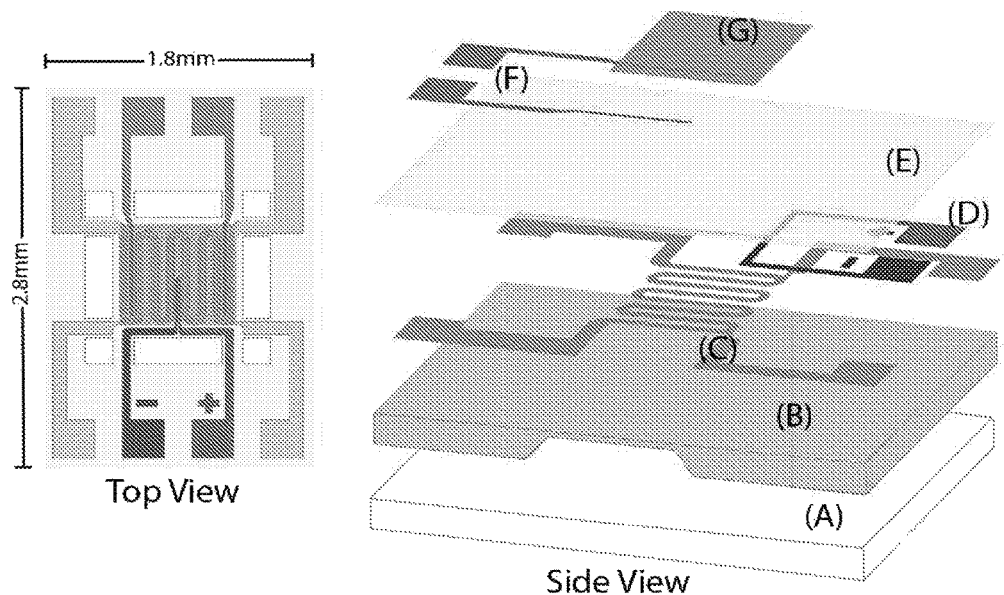
FIG. 15
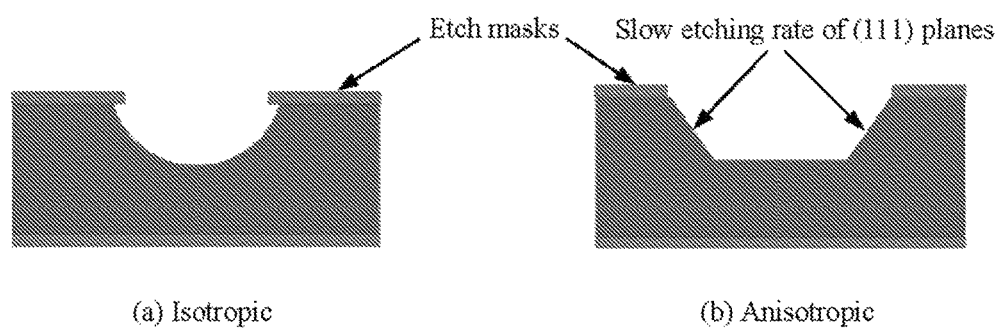
(a) Isotropic
(b) Anisotropic
FIG. 16A
FIG. 16B

SYSTEMS AND METHODS FOR THE DETECTION OF COMPOUNDS

SPONSORSHIP INFORMATION

This invention was made with government support under Grant No. 2013-ST-061-ED0001 awarded by the Department of Homeland Security, Science and Technology. The government has certain rights in the invention.

BACKGROUND

Triacetone-Triperoxide (TATP) is a particularly insidious explosive in that it is very difficult to detect and is frequently used in IEDs because of its relatively simple synthesis from commonly found precursors. TATP readily sublimes at room temperature and thus, is found at relatively high concentrations in the vapor phase relative to other explosives commonly found in IEDs. However, it is difficult to detect using conventional explosive detection techniques because the detection schemes were developed for nitrogen-based chemistries and not peroxide-chemistries.

SUMMARY

In accordance with an embodiment, the invention provides a gas sensor system for detection of a compound that decomposes upon exposure to a metal oxide catalyst. The gas sensor system includes a sensor that includes a microheater, and a metal oxide catalyst that covers the microheater. The gas sensor system includes a pre-concentrator upstream from the sensor that lowers the limit of the detection of a compound.

In accordance with another embodiment, the invention provides a method for detecting a compound using a gas sensor system, wherein the compound decomposes upon exposure to a metal oxide catalyst. The method includes the step of delivering the compound to a pre-concentrator for a pre-determined period of time. The method further includes the step of initiating compound desorption of trapped compound by heating the pre-concentrator. The method further includes the step of exposing the compound to a microheater covered by a metal oxide catalyst of a sensor. The method further includes the step of measuring a first response using a first portion of the sensor. The method further includes the step of measuring a second response using a second portion of the sensor. The method further includes the step of filtering out heat effects by the sensor to detect the compound.

BRIEF DESCRIPTION OF THE DRAWINGS

The following description may be further understood with reference to the accompanying drawings in which:

FIG. 6A shows an illustrative graphical representation of a conductometric response of a $SnO_2$ catalyst to ammonia nitrate (blue), 2,6-DNT (red) and TATP (green) as a function of temperature; and FIG. 6B shows an illustrative graphical representation of a conductometric response of a ZnO catalyst to ammonia nitrate (blue), and 2,6-DNT (red);

FIG. 7 shows an illustrative graphical representation of a thermodynamic response of a $SnO_2$ catalyst to 2,6-DNT (red) and the simultaneously responding dynamic control (blue);

FIG. 15 shows an illustrative schematic view of a top view (left) and an expanded side view (right) of an orthogonal sensor on a MEMS platform;

FIG. 16A shows an illustrative schematic view of an etched shape using an isotropic etch; FIG. 16B shows an illustrative schematic view of an etched shape using an anisotropic etch;

DETAILED DESCRIPTION

Figure 1:
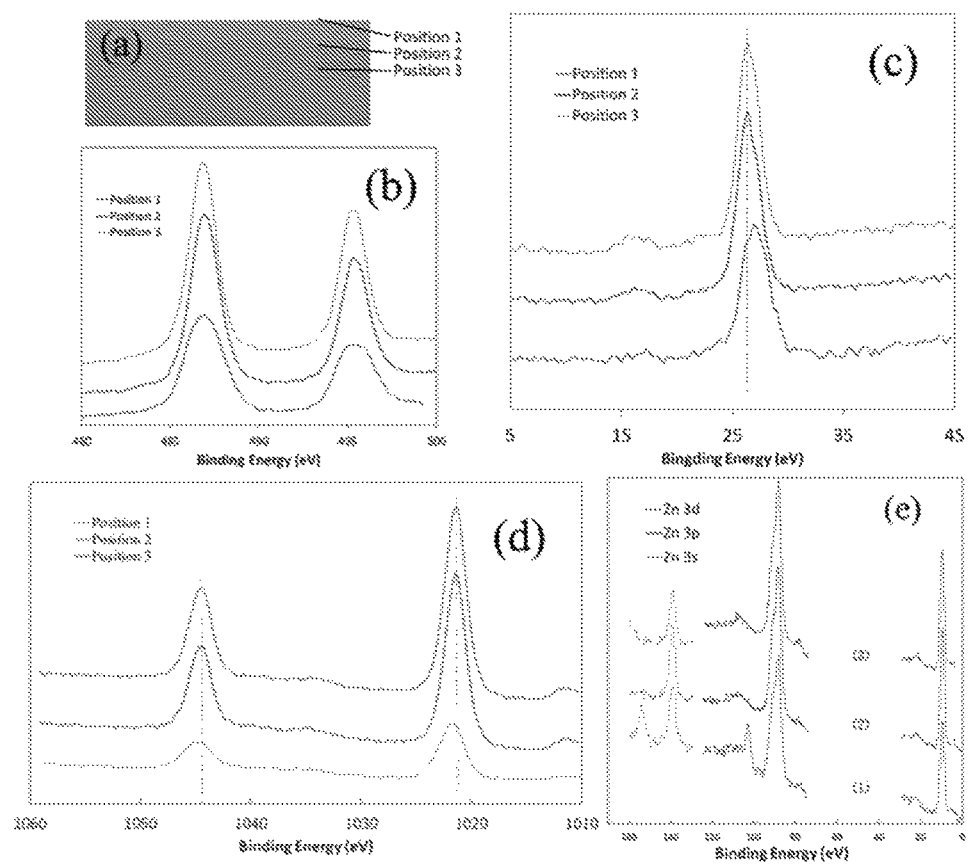
FIG. 1 shows (a) an illustrative graphical representation of the sampling position in a cross-section diagram of $SnO_2$ catalyst; (b) an illustrative graphical representation of X-ray photoelectron spectra (XPS) results of $SnO_2$ catalyst with Sn $3d_{5/2}$ and Sn $3d_{3/2}$ states; (c) an illustrative graphical representation of XPS results of $SnO_2$ catalyst, with Sn 4d states; (d) an illustrative graphical representation of XPS results of ZnO catalyst with the Zn 2p states; and (e) an illustrative graphical representation of XPS results of ZnO catalyst with the Zn 3d, 3p and 3s states.

The present invention overcomes the limitations of previous sensors by improving the selectivity for TATP using combinatorial chemistry techniques to optimize the metal oxide catalyst. By combining a second independent sensing mechanism with a thermodynamic sensing platform, an orthogonal sensor platform was created, whereby a built-in redundancy was incorporated to mitigate false positives. To increase the sensitivity of the sensor, a pre-concentrator device was incorporated upstream from the sensor in an attempt to lower the limit of detection. Finally, in order to miniaturize the sensor and to make it more efficient and sensitive, a MEMS version of the sensor was designed and fabricated. The invention is described in further detail below.

Manufacturing of Orthogonal Sensor

In order to manufacture an orthogonal sensor, a 150 µm high purity alumina cement coating was applied over the serpentine area of a microheater. Both the sputtered alumina film and the thick alumina cement function as insulation layers to prevent the nickel microheaters from direct exposure to gas molecules and to prevent electrical shorts to the marginally conductive oxide catalyst. The cement is polished and the edges are beveled to accommodate the conductometric electrodes that are deposited over the serpentine. Nickel electrodes were deposited over the alumina cement using an MRC 822 sputtering system. The additional electrodes were used to measure the change in electrical resistivity of the metal oxides when exposed to the target gas. $SnO_2$ and ZnO were subsequently deposited using a MRC 8667 sputtering system in pure argon, which produced a non-stoichiometric oxide. Both catalysts were then annealed at 450° C. in nitrogen for 5 hours, densifying the film, eliminating point defects and releasing trapped argon. This was followed by a second heat treatment in a nitrogen/oxygen atmosphere (volume ratio of 95:5) for 5 minutes at the same annealing temperature. The second heat treatment ensured that the surface of catalyst was stoichiometric, favorable for thermodynamic interactions between it and the analyte. Underneath the stoichiometric oxide was a much thicker nonstoichiometric oxide that was tailored for the conductivity measurement. The oxidation states of the metal oxide as a function of depth were characterized using X-ray photoelectron spectroscopy (XPS) to establish depth profiles and confirm the oxidation state in the oxide layer.

For the conductometric half of the orthogonal sensor, a voltage measurement across the semi-conductive $SnO_2$ or ZnO film was recorded using a customized data acquisition system. When target gas molecules contacted the metal oxide, the number of available charge carriers changed, resulting in a corresponding drop or rise in voltage. The same testing protocol described for the thermodynamic sensor was applied here for the conductometric sensor, except the voltage across the conductometric electrodes and the current supplied to the microheater are measured and recorded simultaneously. Sensor responses to explosive vapors as a function of target gas concentration were determined. The sensitivity, detection limit, response time and recovery time for ammonium nitrate (AN), 2,6-Dinitrotoluene (2,6-DNT) and TATP were evaluated for the conductometric platform and thermodynamic platform in the orthogonal sensor.

These particular analytes (TATP, 2,6-DNT and AN) were chosen to evaluate the orthogonal sensor for a variety of reasons. All three explosives belong to different chemical groupings of energetic materials: TATP from the peroxides, 2,6-DNT from the aromatic nitro-group and AN from the acid salts. In addition, TATP and AN were chosen because they are commonly found in homemade explosives and are far more likely to be involved in a terrorist attack. 2,6-DNT, while not as widely used as an explosive in industry as 2,4,6-trinitrotoluene (TNT), is a less dangerous alternative that has similar chemical structure and behavior. Furthermore, DNT is a precursor to the synthesis of TNT; thus, a homemade batch of TNT is likely to contain larger quantities of DNT over the commercially prepared explosive. 2,6-DNT was specifically chosen over its isomer 2,4-DNT because 2,6-DNT has a higher ambient vapor pressure. Finally, these three explosives represent a range of vapor pressures. TATP is a volatile compound and will thus have a high concentration in the vapor phase. 2,6-DNT has a much lower vapor pressure but is still within a detectable range. AN has the lowest vapor pressure and represents a challenge for this vapor detection technique.

The oxidation states of metallic species in the $SnO_2$ and ZnO catalyst were characterized by XPS as a function of depth, as shown in FIG. 1. In particular, (a)-(d) of FIG. 1, position 1, 2 and 3 refer to the as-annealed surface 100 Å and 600 Å below the surface of the catalyst, respectively. The energy states associated with the Sn $3d_{5/2}$ and Sn $3d_{3/2}$ electrons show only slight changes as a function of depth with the exception that both 3d peaks taken at position 1 appear sharper, as shown in (b). When sampled from position 1 to position 3, as shown in (c), a phase transition was observed, during which the Sn 4d peak at 27.2 eV (+4 state) decreased and a shoulder associated with the Sn 4d peak at 26.6 eV (+2 state) increased and eventually formed a new peak. This indicated that a transition from stoichiometric $SnO_2$ at surface of catalyst to a nonstoichiometric $SnO_{2-x}$ had occurred below the surface. From (d), Zn 2p doublets can be observed, indicating that multiple oxidation states exist at the surface of ZnO catalyst most likely due to the oxygen introduced during annealing processes. Also, the Zn $2p_{3/2}$ peaks at positions 2 and 3 shifted to lower binding energies and appear sharper when compared to the peak at position 1, indicating that a uniform $ZnO_{1-Y}$ layer had formed below the surface. This assumption was confirmed in (e) by the disappearance of ZnO secondary peaks corresponding to the 3s and 3p states and an increase in intensity of the 3d peak as a function of position, which was verified as a transition in oxidation state.

Figure 2:
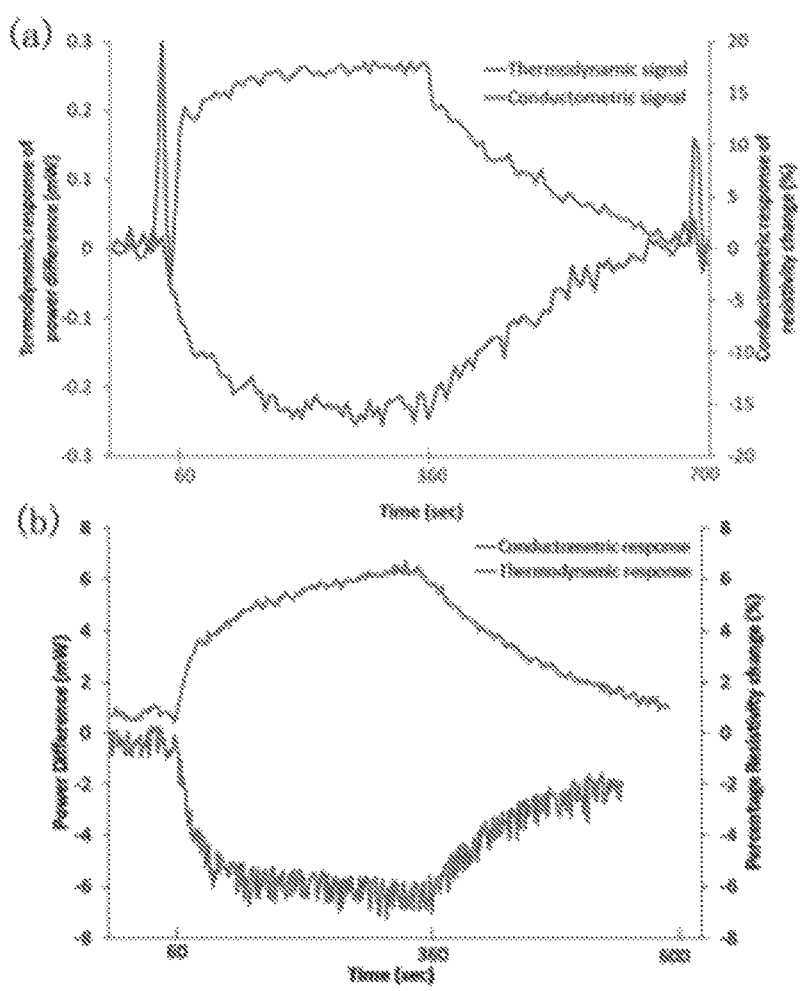
FIG. 2 shows (a) an illustrative graphical representation of a thermodynamic response (blue) and conductometric response (red) to 2,6-DNT at 410° C. taken simultaneously using a $SnO_2$ catalyst from an orthogonal sensor; and (b) an illustrative graphical representation of a thermodynamic response (blue) and conductometric response (red) to 2,6-DNT at 410° C. taken simultaneously using a ZnO catalyst from an orthogonal sensor.

FIG. 2(a) shows a typical response from an orthogonal sensor using $SnO_2$ as a catalyst in the presence of 2,6-DNT. The responses using a $SnO_2$ catalyst are presented in FIG. 2(a) and the responses using a ZnO catalyst are presented in FIG. 2(b), which were initially collected from separate platforms, each individually tuned for optimal thermodynamic and conductometric response. Each sensor was pre-stabilized at 410° C. for 15 minutes before recording data. Then, DNT was introduced into the test chamber after 1 minute for a period of 360 seconds as shown along the horizontal axis in FIGS. 2(a) and 2(b). The sensor employing the $SnO_2$ catalyst exhibited the fastest thermodynamic response time (less than 5 seconds) whereas the conductometric response took significantly longer (60-80 seconds) to reach equilibrium and did not show a sharp transition after introduction of target gas. However, both thermodynamic and conductometric signals completely recovered to the baseline values within 5 minutes. As shown in FIG. 2(b), both the thermodynamic and conductometric signals using a ZnO catalyst demonstrated a rapid response time (less than 10 seconds). However, both responses took a longer time to reach equilibrium and recover, compared to those produced with a $SnO_2$ catalyst.

The difference in response times and recovery times between the two sensing platforms was attributed to their detection mechanisms. The thermodynamic portion or platform measures the heat effect associated with the catalytic decomposition of the target gas, which was initiated instantly as the target gas molecules interact with the surface of catalyst. When additional target gas molecules are introduced, some decomposition occurs immediately. This produces a dynamic equilibrium where the decomposition rate is the rate-controlling step. The conductometric portion or platform measures the charge carrier concentration, which depends on donating or accepting extra charge carriers as the target gas molecule is adsorbed onto or desorbed from the surface of the catalyst. This process also resulted in a dynamic equilibrium where the adsorption and desorption rate is the rate-controlling step. Since the chemical reaction rate is an order of magnitude faster than physical adsorption rate, the thermodynamic signal exhibits a much faster response time and recovery time compared to that of conductometric signal.

Figure 3:
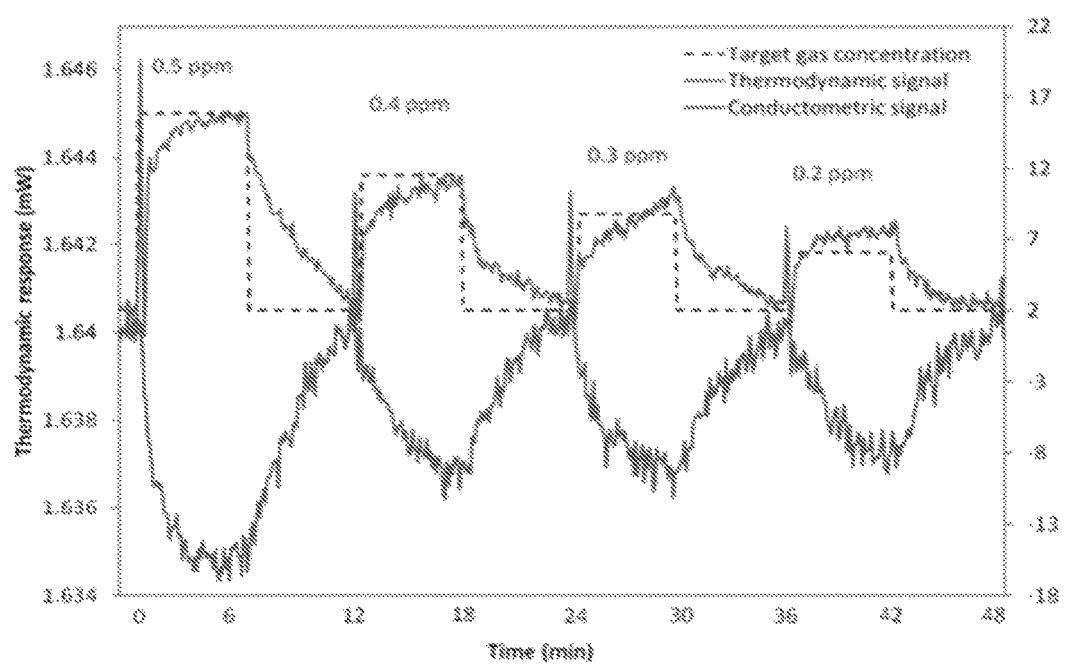
FIG. 3 shows an illustrative graphical representation of a thermodynamic response (blue) and conductometric response (red) of a $SnO_2$ catalyst as a function of 2,6-DNT vapor concentration (black dashed line) at 410° C.

The orthogonal sensor response to 2,6-DNT as a function of DNT vapor concentration (at 410° C. employing $SnO_2$) is shown in FIG. 3. Here, the thermodynamic response was linear with respect to DNT vapor concentration whereas the conductometric response remained the same as the DNT vapor concentration decreased. Both responses were repeatable when the vapor concentration was reduced from 0.5 ppm to 0.2 ppm.

Pre-Concentration

A K-type thermocouple was added to the sensor design to precisely monitor temperature. The sputtered alumina dielectric was deposited over both the microheater and the thermocouple. A polystyrene film was then deposited over a microheater surface using spin coating. Polystyrene beads were dissolved in dichloromethane, forming a viscous liquid. The microheater was masked to protect the electrical contacts and a drop viscous solution was deposited onto the surface and spun at speeds in excess of 500 rpm.

Figure 4:
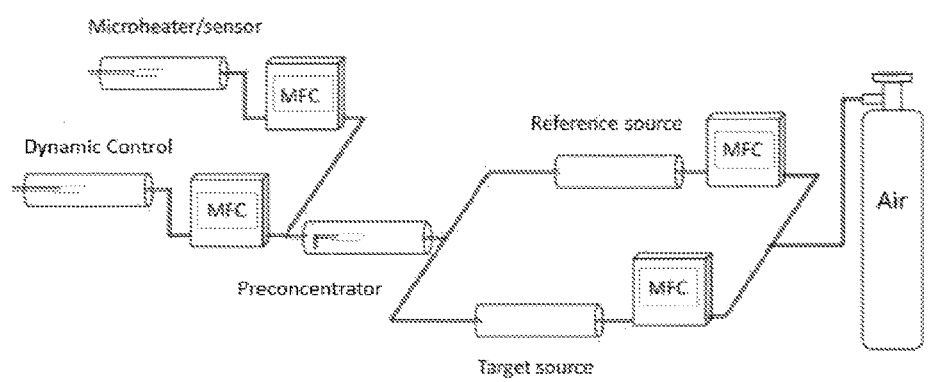
FIG. 4 shows an illustrative schematic view of a piping system.

Immediately upstream from the explosive sample chamber, an additional vessel containing the pre-concentrator was placed into piping system, as shown in FIG. 4. A polymer-coated microheater is placed inside the vessel and acts as the pre-concentration cell. The pre-concentrator must be heated to promote thermal desorption of the collected analyte. Thus, the microheater located underneath the polystyrene was connected to a constant current source and the voltage was measured across the thermocouple to precisely control and monitor the temperature. The added heat upstream from the active sensor element resulted in a power change, independent of any catalyst-analyte interaction. Thus, a method was devised to filter out any extraneous heat changes to isolate catalytic activity.

To accomplish this, downstream from the pre-concentrator, air was siphoned off into two different chambers, precisely monitored with mass flow controllers (MFCs) to ensure that both chambers receive the same volume of air. In one chamber is located a microheater coated with a passivating layer of alumina and a metal oxide catalyst, and the other chamber contains a microheater coated with only a passivating layer of alumina. If the microheaters are identical to one another electrically, the sensor can be operated under dynamic control.

Figure 5:
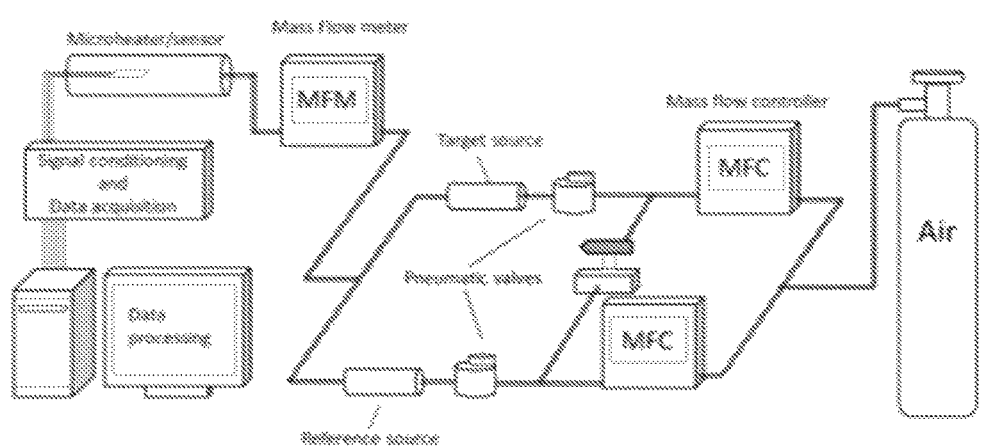
FIG. 5 shows an illustrative schematic view of a testing apparatus.

Both sensors were tested according to the thermodynamic testing protocol, all the while mirroring the other's temperature. The dynamically controlled sensor responds to subtle heat effects such as thermal desorption during pre-concentrator operation, sensible heat effects, adsorption heat effects to the alumina dielectric and flow rate changes. The catalyst coated sensor detects some of these same heat changes plus the heat change associated with any catalyst-analyte interactions; thus by subtracting the two signals, the extraneous heat effects are filtered out, completely isolating the sensor response due to catalytic activity. A schematic of this testing apparatus is shown in FIG. 5. The data acquisition system was interfaced to a computer and controlled using LabView software. After reaching each target set point temperature, the sensor was allowed to equilibrate for 360 seconds under constant inert gas flow. The target gas was then introduced from a target source into the test chamber for 180 seconds and then the reference gas was introduced from a reference source for 180 seconds before the microheater was ramped to the next temperature set point. Because it is critical for the catalyst coated sensor and the dynamic control sensor to respond similarly to these extraneous heat effects, individual sensors were pre-screened for similar electrical and thermal properties and paired prior to testing.

Several single-step tests were conducted in this apparatus. Referring back to FIG. 4, air was passed over the pre-concentrator and delivered to the sensor chambers for 60 seconds as a reference. Then, target molecules were delivered to the pre-concentrator and the sensor for 180 seconds. During this time, the pre-concentrator was in a "collection phase", meaning the polystyrene film was maintained at room temperature in order to allow any target explosive molecules to adsorb to the polymer surface. After the 180 seconds, current was applied from a current source to the microheater to rapidly heat the polymer film to 95° C., allowing desorption to occur. This temperature is below the glass transition temperature of polystyrene, thus not warm enough to cause the polymer film to begin to flow. Analyte desorption continues for an additional 120 seconds, then the constant current source was turned off, allowing the pre-concentrator to passively cool. Then, reference air is passed through the system to observe the sensor's recovery time.

The conductometric response to ammonium nitrate, DNT and TATP vapor as a function of temperature employing $SnO_2$ and ZnO as catalysts are shown in FIGS. 6A and 6B, respectively. The responses of both catalysts to ammonium nitrate was proportional to temperature at low temperature ranges (<250° C.) and then decreased with temperature as it was raised over 350° C. 2, 6-DNT showed similar behavior relative to ammonium nitrate but only exhibited a shallow peak at 280° C. with both catalysts. The TATP signal produced from the $SnO_2$ catalyst changed very little with temperature, whereas the sensors employing ZnO catalyst did not show a conductometric response to TATP and therefore, were not included here. These differences in sensor response were attributed to the differences in vapor pressure of target molecules and differences in the functional groups and molecular structures between the target molecules. However, the exact mechanism remains unknown due to the complexity of the processes. As a result, all three compounds (TATP, DNT and ammonium nitrate) exhibited unique signatures (orthogonal responses), which could be used to further characterize their presence and mitigate false positives and negatives.

Before the pre-concentrator is discussed in detail, it is worth detailing the benefits of using a dynamic control sensor to eliminate extraneous heat signals. For example, FIG. 7 shows a single step test at 400° C. for 2,6-DNT using a stoichiometric $SnO_2$ catalyst. The step response from the catalyst microheater is plotted on the same axes as the response from the control, and it can be observed that the catalyst response is much larger. Both the dynamic control and the catalyst coated sensor responds to the adsorption and desorption of molecules on the alumina surface. Adsorption can either be chemi-adsorption, the result of a covalent bond between the adsorbent and the analyte causing a relatively large heat effect, or physical-adsorption, the result of weak van der Waals attractions causing a relatively smaller heat effect. Alumina is mostly non-reactive thus will likely physically adsorb any analytes or vapors.

Another contributing thermodynamic effect is the sensible heat effect change that occurs when the explosive vapors are introduced to the sensor. Though the explosive vapors are only present at trace levels, the heat capacity of many of these energetic materials are so large relative to that of air, that the change can be detected by the thermodynamic sensor. If the incoming gas to the sensor is considered as a "coolant," the air containing trace explosive molecules is a better coolant than pure air and thus, the sensor will require only slightly more power to maintain a constant temperature. A small contributing heat effect could also be due to the presence of nickel oxide on the surface of the microheater. Previous study has shown that NiO reacts with a few target explosives, and can form on the surface of the microheaters after sputtering before it is coated with the dielectric. Although, any NiO present is embedded under alumina cement and is unlikely to be a major contributing thermodynamic factor.

That leaves the catalyst-coated sensor only to catalytically react to the analyte, resulting in a larger thermodynamic signal than that of the dynamic control. Thus, when determining the power difference at this temperature set point, the crest of the dynamic control response is used as a baseline instead of the power requirements during the flow of pure air. Signatures that can be used to identify a particular explosive using a particular catalyst can now be obtained with more clarity because the pure catalytic heat effects can be isolated.

Figure 8:
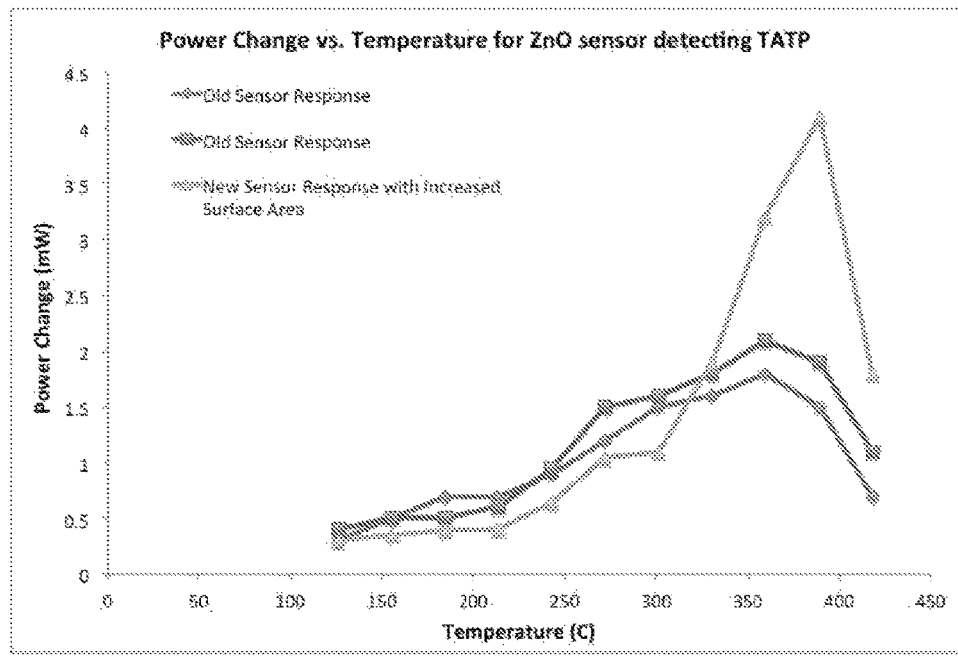
FIG. 8 shows an illustrative graphical representation of a thermodynamic signal of a ZnO catalyst with and without the dynamic control and increased surface area catalyst)

FIG. 8 shows one such signature obtained for TATP using a ZnO film. On the same axes are signatures from two different sensors that do not have the benefit of dynamic control as compared with the signals using dynamic control with increased surface area catalyst support. Between 125° C.-300° C., the new signature falls below the previous signature, indicating that there are heat effects that the old signal is accounting for that are indeed filtered from the latest result. Also, there is a very pronounced peak at 375° C., much larger in magnitude than before. The resolution of this peak is due to the use of a dynamic control to filter out the extraneous heat signals, but the magnitude change was due to an increase in the surface area of the catalyst (using a more porous aluminum oxide support).

An added benefit of this approach is the enhancement in sensitivity due to the high surface area of the alumina cement. The primary purpose of the cement was to serve as a dielectric to prevent electrical shorts between the Ni microheater and the semi-conductive catalyst film. In the orthogonal sensor, Ni electrodes were placed on top of the cement as well, making it necessary to polish the cement surface and bevel the edges to make the surface conducive to deposition by sputtering. In these thermodynamic sensors used for evaluation of the dynamic control, the cement films were left as is, remaining highly porous.

Figure 9:
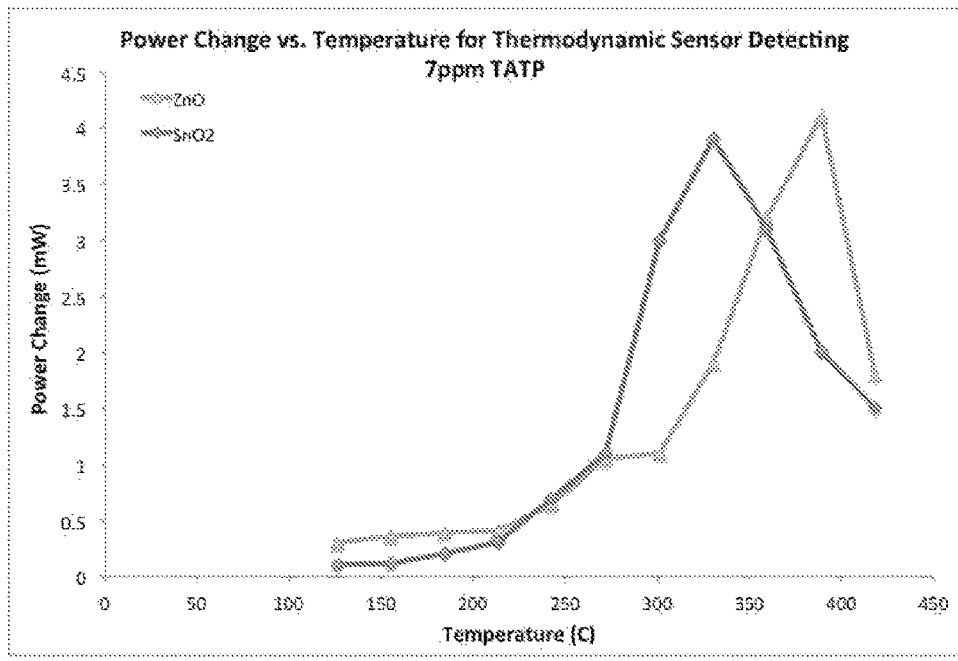
FIG. 9 shows an illustrative graphical representation of thermodynamic signatures of $SnO_2$ (blue) and ZnO (green) to 7 ppm TATP.

Also, it is the nature of sputtered films that they coat the surface of the substrate, preserving any and all surface features. The result was a high-surface area catalyst surface with a much higher density of catalytic sites, directly improving sensitivity. Testing with these sensors yielded a large increase in magnitude of the thermodynamic signal for testing with ZnO and $SnO_2$, as seen in FIG. 9. An interesting feature of this plot is the shift in peak placement in the signature for each catalyst. The peak occurs at 375° C. with ZnO, but using $SnO_2$ the peak occurs at 325° C. This peak corresponds to the largest catalytic heat effect, and because it occurs at different temperatures for different catalysts, it reinforces that these signals are unique and can be used to identify an unknown vapor as TATP.

Figure 10:
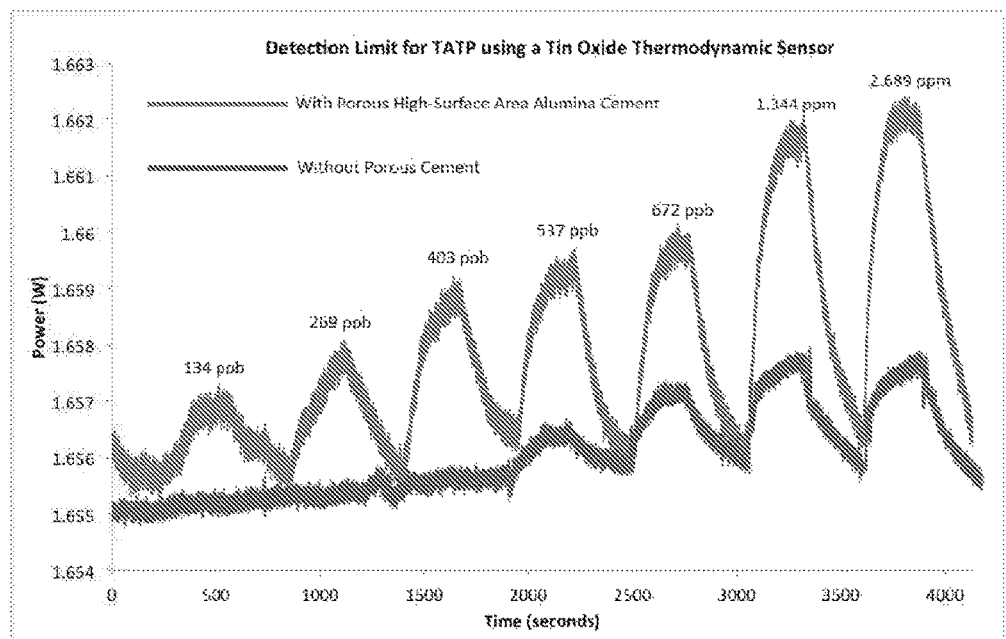
FIG. 10 shows an illustrative graphical representation of a concentration test illustrating the detection limit of TATP using a $SnO_2$ catalyst.

Finally, a concentration test was conducted using $SnO_2$ to determine if the detection limit for TATP had changed, as shown in FIG. 10. Without the alumina cement, the sensor was able to detect TATP at 537 parts per billion (ppb), but with the enhanced surface area, the detection limit was reduced to 134 ppb.

Figure 11:
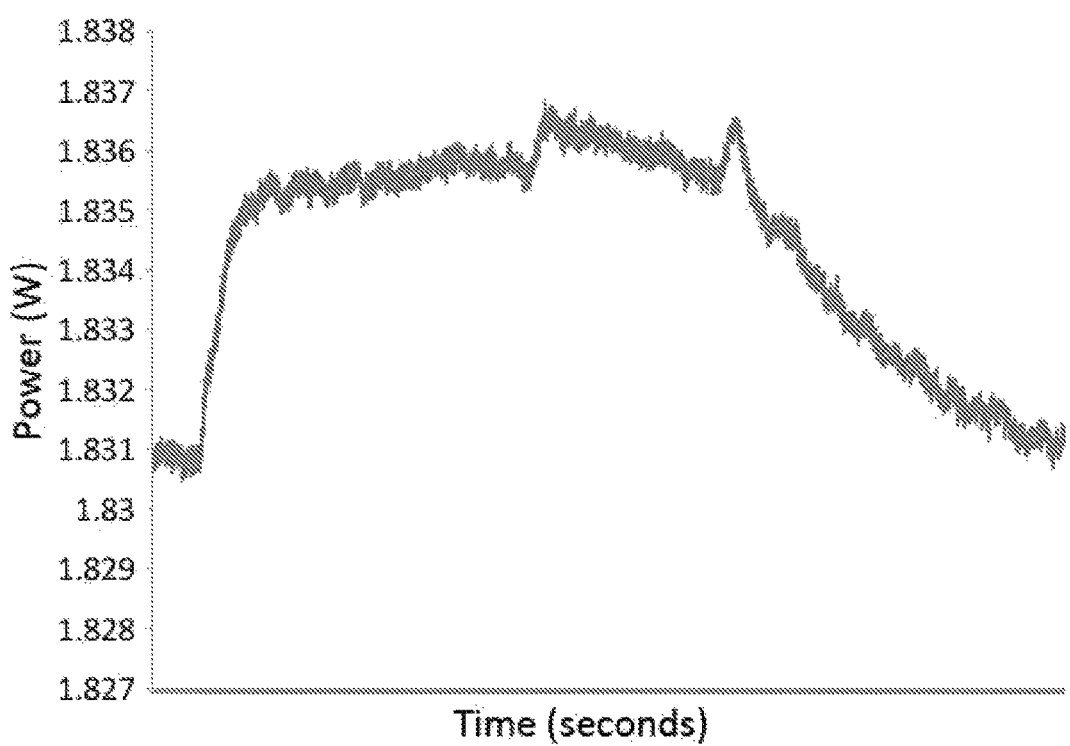
FIG. 11 shows an illustrative graphical representation of a pre-concentration test conducted using a stoichiometric $SnO_2$ catalyst and 2,6-DNT.

The first polystyrene pre-concentration test was conducted using a stoichiometric $SnO_2$ catalyst and 2,6-DNT, resulting in the step response in FIG. 11. The polystyrene film used in this test was measured to be approximately 10 µm. Partway through the step, a small peak is observed, corresponding to the start of the pre-concentrator's desorption phase. The power change as a result of these pre-concentrated molecules was small. However, the expected power change as a result of the added heat from the pre-concentrator was expected to be negative. The fact that the direction of the response is positive led to the determination that a method to filter out the thermal desorption heat effects was necessary to resolve any increase in sensitivity.

Figure 12:
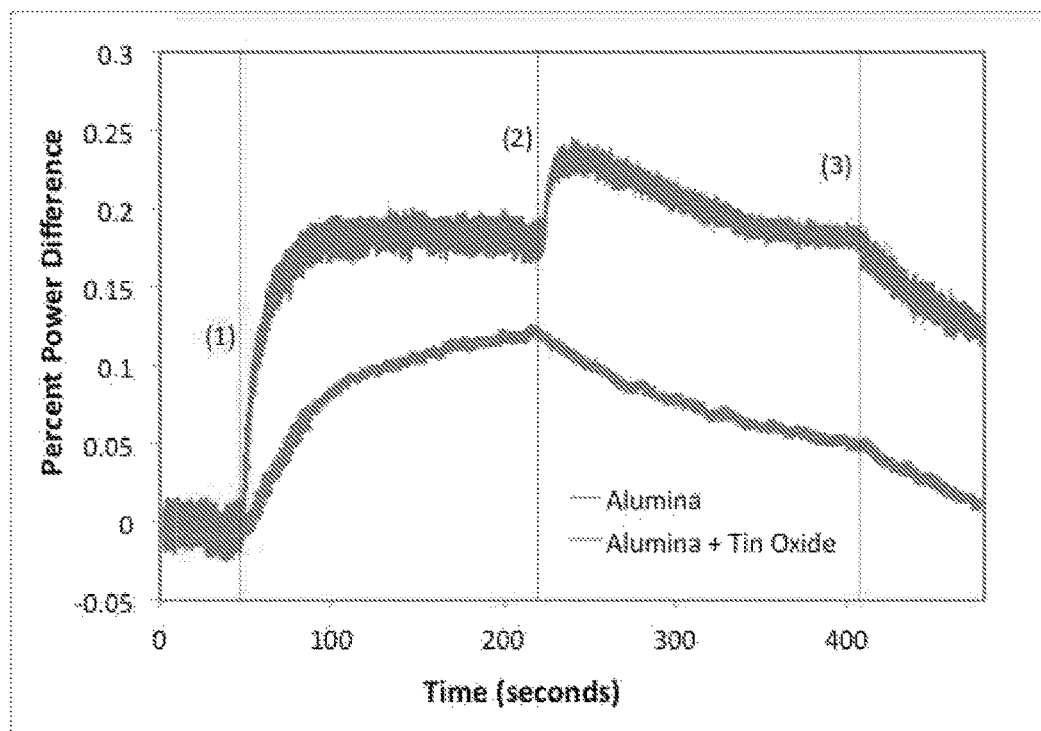
FIG. 12 shows an illustrative graphical representation of the results of a pre-concentration test conducted using a stoichiometric $SnO_2$ catalyst and 2,6-DNT using the dynamic control method: (1) beginning of DNT delivery to sensors; (2) beginning of thermal desorption by pre-concentrator; (3) turning off pre-concentrator and reintroducing reference gas.

Implementing a dynamic control sensor along with the $SnO_2$ sensor, and conducting the same experiment with DNT, yielded the signal seen in FIG. 12. The signal on top is from the catalyst coated sensor and closely resembled the sensor response in FIG. 11. However, the signal on the bottom from the dynamic control sensor shows the negative change in power associated with the thermal desorption phase of the pre-concentrator. There are three significant changes in the signal, each occurring at different time points as indicated in FIG. 12 that are denoted by the numbers (1), (2), and (3). Change (1) is the point which marks the beginning of DNT delivery to both the pre-concentrator and the sensors further downstream. During this time, the pre-concentrator was collecting DNT molecules and was thus maintained at room temperature. Change (2) is the point which indicates when the pre-concentrator is heated from 20° C. to 97° C. to begin the thermal desorption of the trapped DNT molecules. At this point, the dynamic control exhibits a downward power change, responding to the rise in the temperature of the incoming air, which is expected. The catalyst-coated sensor exhibits a positive change, indicating that more DNT is reaching the catalyst surface, thereby increasing the magnitude of the response. Finally, change (3) is the point at which the pre-concentrator is turned off and reference gas is reintroduced to the chamber and the beginning of the recovery phase.

Using this dynamic control method, the extraneous heat activity, which now encompasses the thermal desorption of the pre-concentrator, can be filtered from the catalyst signal. The new power change is determined by measuring the difference between the power of the catalyst sensor signal between points (2) and (3) and the power of the dynamic control in that same interval. It can be seen on this signal that using the pre-concentrator increases the magnitude of this power difference, from 0.1% to 0.15%.

Additional tests were then conducted, using the same testing protocol and sensor configuration while varying some key test parameters. A second pre-concentrator, with a much thinner polystyrene film, was interchanged with the first. The thickness was measured to be less than 1 μm. It was expected that the decrease in thickness of the adsorbent film would lower the retention volume, thus resulting in a smaller thermodynamic signal during thermal adsorption. What was observed was no significant change in the magnitude of the thermodynamic signal, indicating that the retention volume of the sorbent was independent of the thickness of the film. The spin-coated polymer films are likely dense and nonporous, only allowing the adsorption of molecular species on the planar polymer surface.

Figure 13:
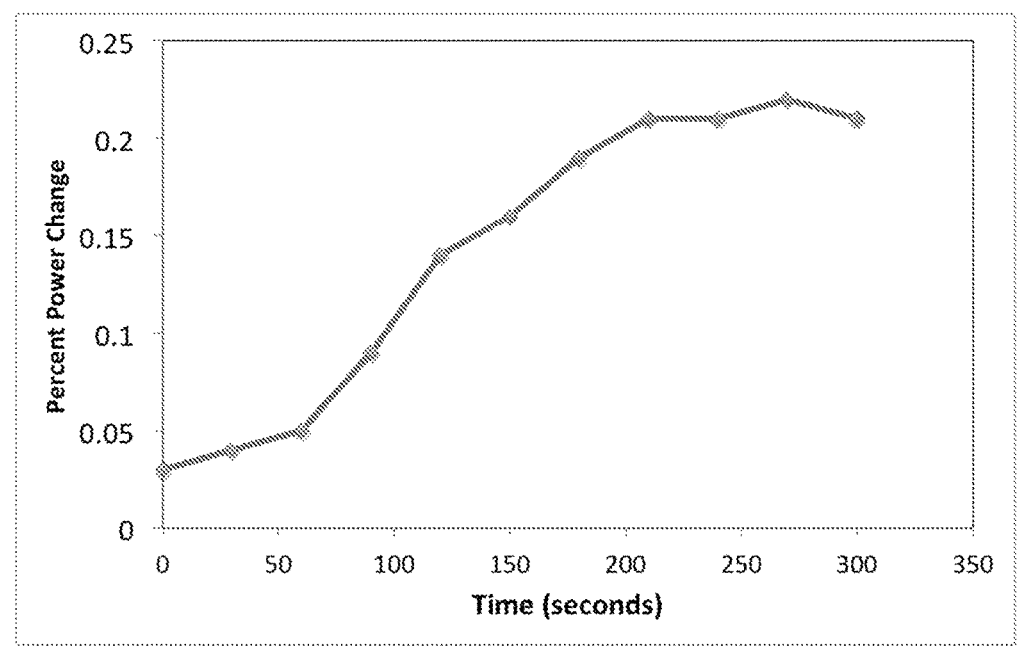
FIG. 13 shows an illustrative graphical representation of the effect of pre-concentrator collection time on the magnitude of the thermodynamic sensor response.

It was then hypothesized that shortening or lengthening the collection time would decrease or increase the thermodynamic sensor response respectively. FIG. 13 shows the effect of collection time on the magnitude of the change. At low collection times, the relationship is almost linear indicating that longer collection times result in proportionally larger responses. This was true until collection was allowed to occur for 200 seconds or longer. Increasing the time any further yielded diminishing returns. It appears that after 200 seconds of collection, the adsorption sites on the polystyrene film are all occupied and the film becomes saturated. It is also worth noting that at point time=0, there is a power difference between the two sensors. This is likely due to heat losses that occur in the distance between the pre-concentrator and the sensor chambers.

Figure 14:
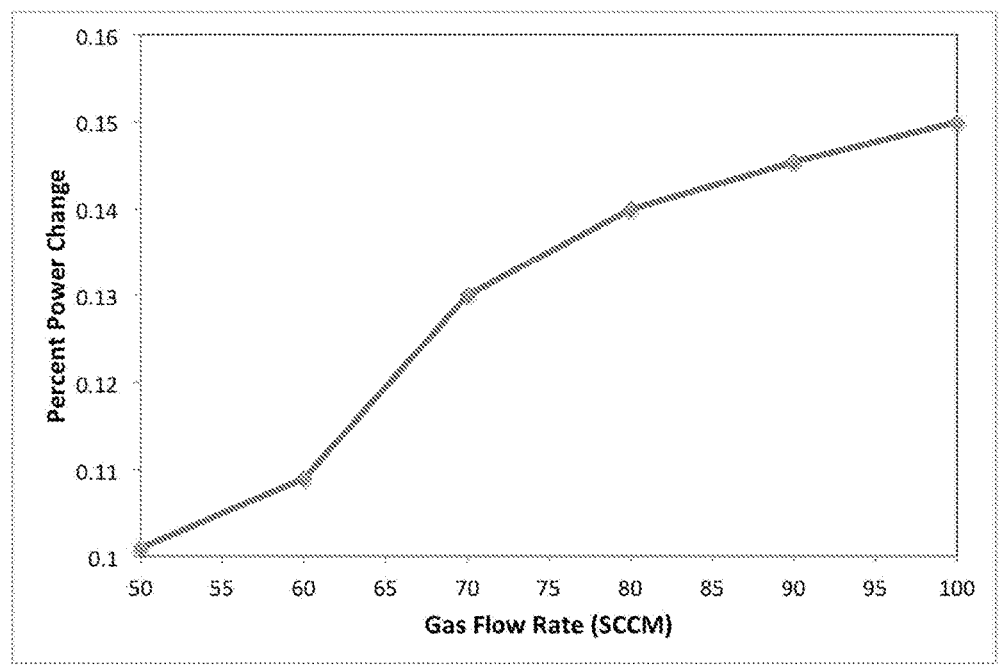
FIG. 14 shows an illustrative graphical representation of the effect of flow rate on the magnitude of the thermodynamic sensor response.

Some sources also report that flow rate is an important factor in the adsorption process. FIG. 14 shows different power changes recorded at different flow rates. It was important for this test to vary the flow rate, but maintain the same volume of air that passes over the sensors. For instance, when the flow rate was at 100 sccm, the collection period lasted 2 minutes. When the flow rate was reduced to 50 sccm, the collection period was lengthened to 4 minutes, making the total volume (and thus total amount of analyte) the same in both experiments. The result was a proportional relationship between the flow rate of the gas and the resulting thermodynamic signal. Several sources indicate that the increased pressure in the pre-concentrator favors the adsorption process. This is a positive result for pre-concentration because it indicates that in order to accelerate the adsorption process, the flow rate could be increased. The pre-concentrator geometry in this case is also such that not every analyte molecule comes in contact with the adsorbent film and is captured. If an increased flow rate could be paired with a pre-concentrator design that ensured contact with a greater percentage of the incoming air, a larger increase in response would be observed.

Other analytes were also tested to determine any and all changes in preconcentrator design. Out of all the analytes tested, 2,6-DNT had the most dramatic results, and this agrees with many sources that indicate polystyrene has a high affinity for nitroaromatic compounds. Tests were conducted with both TATP and AN as the analyte. TATP did adsorb to the polymer surface, however the resulting increase in power difference during thermal desorption was less than 0.05%, suggesting either a low adsorption or desorption rate for TATP using polystyrene. AN did not show any measurable response, even at large collection times, confirming many sources that indicate ammonium nitrate adsorbs with great difficulty.

Overall, the pre-concentrator was successful in increasing the sensitivity of the sensor. At the same target gas concentration, the magnitude of the sensor response increased from 0.1% to 0.15%. The dynamic control method is also successful on its own and will likely be a fixture in all of the experimentation moving forward. As it stands based on these experiments, the pre-concentrator can be operated successfully in a semi-continuous process, albeit with a longer than desired time constant. When considering the practical application of this method, a timing scheme could be developed that cycles the pre-concentrator between collection and desorption repeatedly. FIG. 11 indicated that a maximum analyte retention occurred at collection times as low as 200 seconds, and 120 seconds would be a reasonable amount of time to desorb enough analyte to illicit a response. In addition, time must be allowed for the pre-concentrator to cool back to its collection temperature, which it currently does passively in approximately 60 seconds. The attractiveness of this vapor sensor, in general, is the potential for instantaneous results; thus, adding a waiting period totaling more than 4 minutes between results is undesirable. To implement this pre-concentrator in real time, steps will have to be taken to reduce the collection time and to boost the retention volume of the adsorbent. This could be done by increasing the size and changing the geometry of the pre-concentrator chamber to optimize the duty cycle.

These experiments also reveal that the pre-concentrator requires a specific adsorbent to attract a specific analyte. Polystyrene was only successful in adsorbing, 2,6-DNT, but a different sorbent could easily be implemented in its place. Polystyrene also has a thermal limitation. Its glass transition temperature at 100° C. places a restriction on thermal desorption, however, some sources indicate that higher temperatures are necessary for more complete desorption of collected DNT. Spin coating the polystyrene also resulted in a dense film that was evidently only capable of surface adsorption.

MEMS-Based Sensors

The main purpose of transferring the sensor platform to MEMS based platform was to produce a smaller footprint that consumes less heat. In addition to the thermodynamic sensor and conductometric sensor, a K-type thermocouple was incorporated into the MEMS system to monitor temperature activity. A schematic of a top view of an orthogonal sensor on a MEMS platform is shown in FIG. 15, with another view showing an expanded side view of an orthogonal sensor on a MEMS platform. With respect to the expanded side view, the components of this view include (A) pyrex substrate, (B) silicon wafer, (C) nickel microheater, (D) type K thermocouple, (E) silicon oxide layer, (F) platinum electrodes, and (G) metal oxide catalysts. The fabricated dimension of MEMS platform was 2.8 mm×1.8 mm×0.7 mm. One of the most important processes involved in the fabrication was etching processes, which was used to create a suspended plane (1 mm×1 mm×5 μm) which was supported by tiny bridges (0.1 mm×0.1 mm×5 μm) to reduce heat sink.

Figure 17:
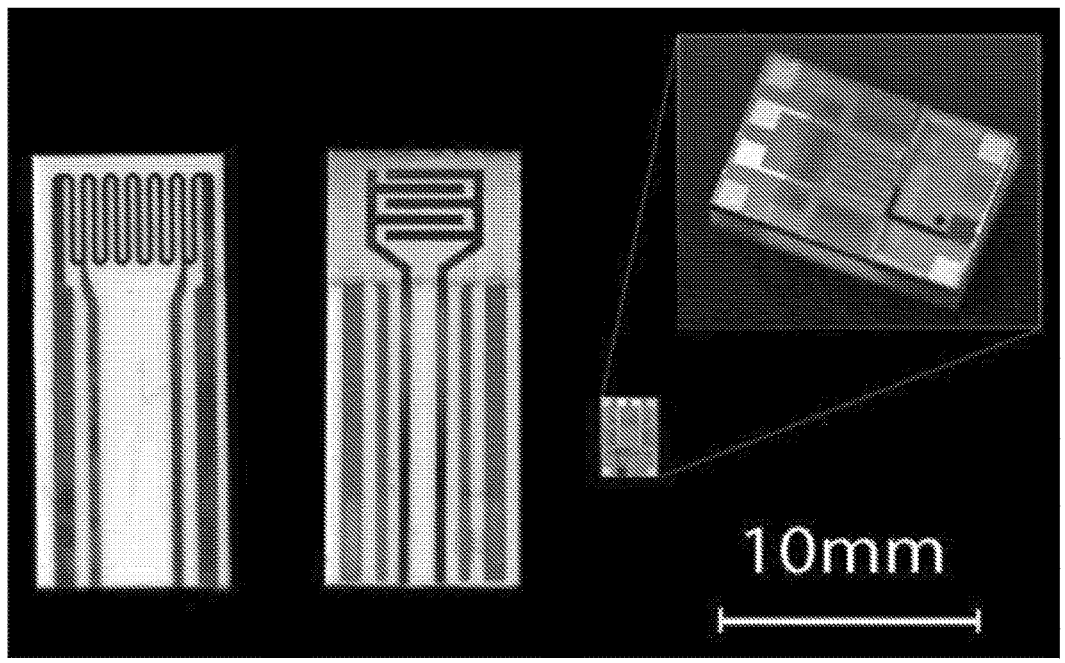
FIG. 17 shows illustrative photographs comparing the relative sizes of the solid state thermodynamic sensor (left), a solid state orthogonal sensor (center), and the MEMS design (right)

A 1.5 μm $SiO_2$ layer was thermally grown on both sides of the oriented silicon wafer through by heating at 1000° C. for 48 hours. FIG. 16A shows an illustrative schematic view of an etched shape using an isotropic etch. The wafer was then patterned using a positive photoresist and windows were etched into the $SiO_2$ using a hydrofluoric acid (HF) and ammonium fluoride ($NH_4F$) etchant. Since formation of extra hydrogen ions is impeded by $NH_4F$, this etching solution favored the etching of $SiO_2$ over Si. The photoresist was lifted off and a potassium hydroxide (KOH) etch was used to etch anisotropically into the Si at an elevated temperature resulting in the shape seen in FIG. 16B. The remaining thickness of Si was estimated to be less than 10 µm. A pyrex wafer was then anodically bonded to the Si wafer to fortify the substrate, forming a cavity in between the two wafers. Using photolithography and RF plasma sputtering, Ni microheaters and a type-K thermocouple were then deposited onto this reinforced wafer, followed by a $SiO_2$ insulation layer on top. Pt conductometric electrodes and a metal oxide catalyst layer were then sputtered over the $SiO_2$ insulation layer. Windows were etched to further reduce the thermal mass of the suspended plane using a third etchant, tetramethylammonium hydroxide (TMAH, $(CH_3)_4NOH$). Finally, the wafer was diced resulting in the finished MEMS sensor depicted in the rightmost part of FIG. 17.

Figure 18:
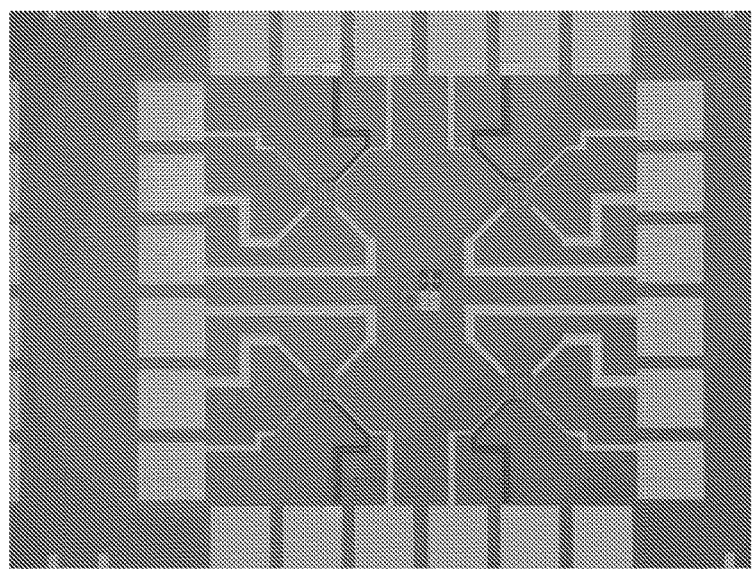
FIG. 18 shows an illustrative schematic view of a MEMS design in accordance with an embodiment of the invention, incorporating four sensors to one 5 mm by 5 mm chip.

A second MEMS design was also produced using MEMs fabrication techniques, as depicted in FIG. 18. This particular iteration incorporates four thermodynamic sensors with individual thermocouples onto one chip, allowing for the implementation of several different catalysts at once, or even a dynamic control. Each microheater is a Ti/Ni composite on top of Ti/Au bond pads and the active area is 0.25 mm×0.25 mm, over 10 times smaller than the active area of the microheater in the single sensor MEMS design, providing an even smaller thermal mass. The membrane is also constructed using a stack of plasma-enhanced chemical vapor deposition (PECVD) films (150 nm $SiO_2$/100 nm $Si_3N_4$/100 nm $SiO_2$) and then back etched with xenon difluoride ($XeF_2$).

TABLE 1

Comparing the heat requirements for all three sensor platforms.

| | Solid State | Previous MEMS | New MEMS |
|---|---|---|---|
| Energy required to heat from 20° C. to 400° C. | 72.35 J | 1.178 J | 0.079 J |
| Power required to maintain 400° C. | 1.410 W | 1.97 mW | 0.495 mW |
| Catalyst area | 0.33 $cm^2$ | 0.01 $cm^2$ | $6.25 \times 10^{-4}$ $cm^2$ |

Figure 19A:
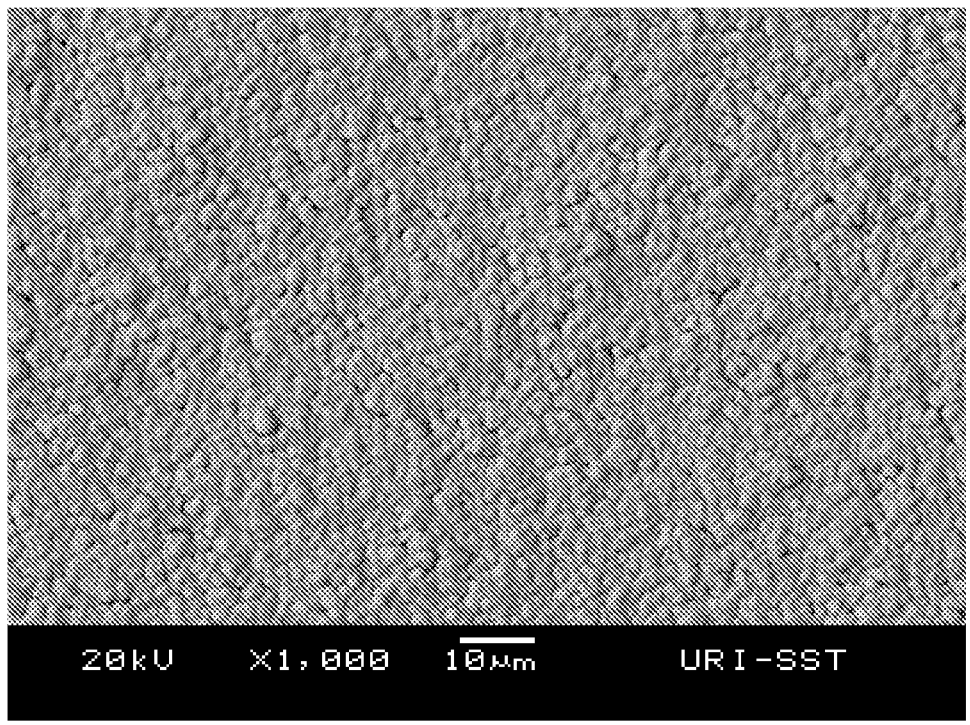
FIG. 19A illustrates a scanning electron micrograph (SEM) of a sputtered zinc-oxide catalyst.
Figure 19B:
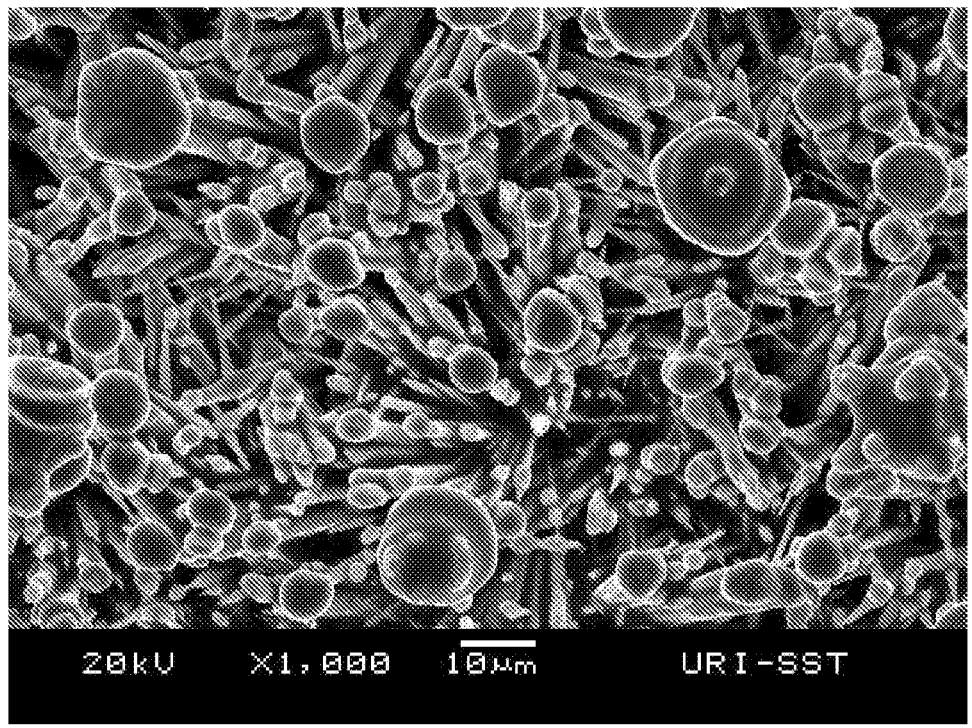
FIG. 19B illustrates a scanning electron micrograph of a zinc oxide nanowire catalyst.

Table 1 summarizes the estimations of the previous sections. These calculations exclude heat losses due to radiation and the conduction heat loss in the horizontal direction (across the suspended bridges in the MEMS), but it is a reasonable assumption that the largest heat loss is due to natural convection, and that is the means of comparison here. The results indicate that the MEMS sensors consume considerably less power than their solid-state counterpart. Furthermore, the newest iteration of the MEMS sensor consumes even less power, due to thinner membranes, a smaller active surface area and an overall smaller thermal mass. It will be noted, however, that the smaller active surface area of the microheater on the MEMS devices are orders of magnitude smaller than the solid state device. The catalyst film on the solid-state sensor also has the benefit of the porosity of the alumina film underneath it, increasing surface area further. The MEMS catalyst would be featureless and planar (FIG. 19A) as compared to the surface area attainable with nanotechnology (FIG. 19B). Results from a previous section in this application indicate that surface is a crucial feature of a catalyst film to ensure sensitivity. It is unclear whether the measured surface listed in Table 1 would be substantial enough to illicit a sensor response, even considering the expected rise in the sensitivity that comes with a drastically reduced thermal mass.

Zinc Oxide Nanowire Catalyst and Catalyst Support

As previously mentioned, surface area of the catalyst is critical to its activity and performance, which greatly impacts the sensitivity of the gas sensor. When moving the sensor platform from a solid state sensor (based on alumina substrates) to a MEMS-based sensor fabricated on free standing silicon nitride diaphragms, the overall surface area will be decreased due to the reduced footprint. In order to maintain the performance of the MEMS-based sensor relative to the solid state sensor, without sacrificing available surface area, zinc oxide nanowires will be fabricated directly onto the free-standing silicon nitride diaphragms. The zinc oxide nanowires, as shown in FIG. 19B, provide more than six orders of magnitude increase in surface area relative to the sputtered catalyst films as shown in FIG. 19A.

Figure 20:
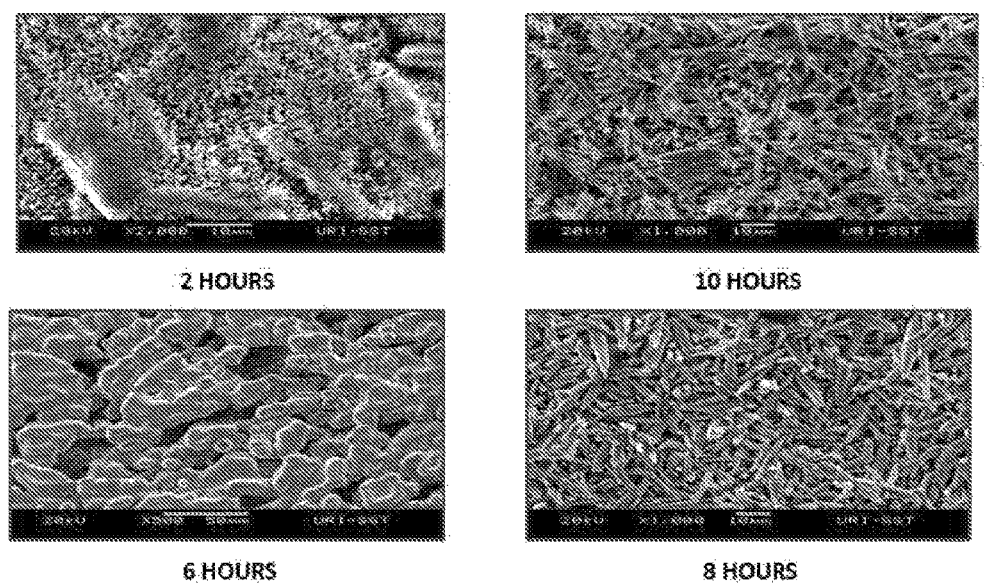
FIG. 20 shows a plurality of SEMs showing the growth sequence of zinc oxide nanowires as a function of time.

Currently, the fabrication sequence used to form ZnO nanowires on alumina for the solid-state sensors is as follows: high purity zinc foil (99.9% purity) is submerged in a 3.5M aqueous solution of ethylenediamine, maintained at 140° C. in an autoclave for 10 hours. A sequence of SEM micrographs showing the growth of the zinc oxide nanowires as a function of time is shown in FIG. 20. After the growth process is complete, the foil is allowed to cool to room temperature before being applied to the sensor surface. The nanowires are scraped from the zinc foil and deposited onto the alumina cement that covers the nickel microheater surface. The nanowires have multiple benefits; not only do they dramatically increase the effective surface area of the sensor, but they also decrease the minimum detection limit of explosives. This in turn will allow the sensor to detect a wider range of explosives not previously possible due to their characteristically low vapor pressures.

Figure 21:
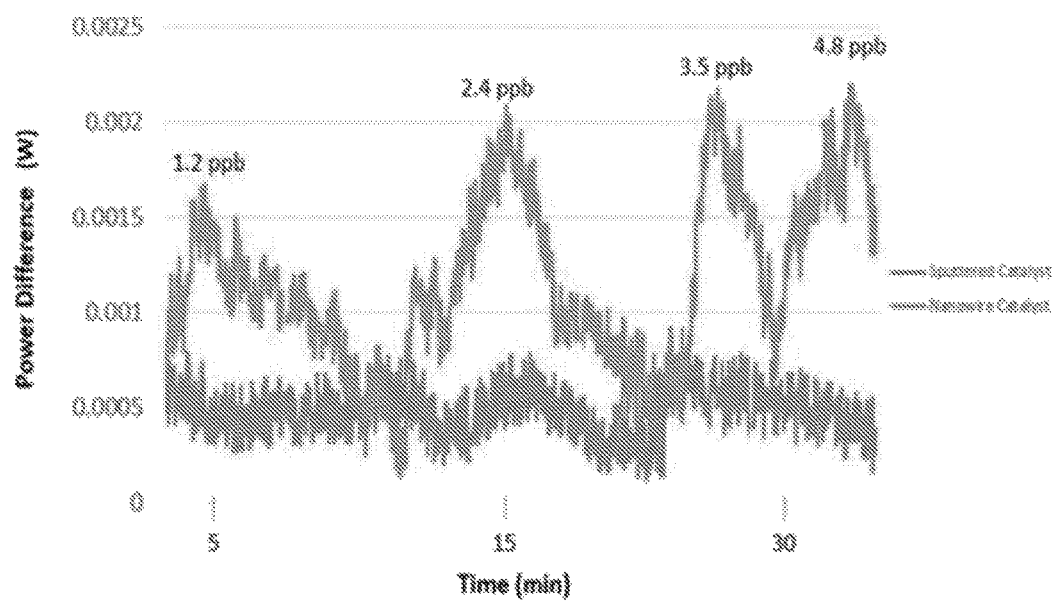
FIG. 21 shows an illustrative graphical representation of a concentration test comparing the power difference of a sensor fabricated with and without zinc oxide nanowires when exposed to 2,6-DNT.

Further improvements to sensor performance using the zinc oxide nanowires been demonstrated as shown below in FIG. 21. Not only can the nanowires be used as the catalyst but also can be used as the catalyst support whereby a wide variety of oxides can be directly deposited onto the zinc oxide nanowires to improve the sensor's detection ability; i.e. the zinc oxide nanowires in this application are primarily used as a catalyst support to gain surface area advantage. By sputtering various oxide films over the microheater-coated surface that is covered with zinc oxide nanowires, the surface area will be optimized while pairing the analytes with their ideal catalyst.

Concentration tests were completed that confirm the effect of surface area on sensor sensitivity and detection limit. For example, sensors fabricated with a sputtered tin oxide film were tested against sensors fabricated with zinc oxide nanowires prior to being sputtered with a tin oxide film, as shown in FIG. 21.

When exposed to 2, 6-DNT, the sensor fabricated with zinc oxide nanowires and sputtered tin oxide catalyst, not only decreased the detection limit to 1.2 ppb, but also increased the magnitude of the sensor response by nearly 300%. By utilizing the zinc nanowires for their surface area, the sensitivity was greatly increased in comparison to a sputtered catalyst film. The increase in response should allow achievement of detection limits in the parts per trillion (ppt) level, which had yet to be accomplished.

Those skilled in the art will appreciate that numerous modifications and variations may be made to the above disclosed embodiments without departing from the spirit and scope of the invention.

What is claimed is:

1. A gas sensor system for detection of a compound that decomposes upon exposure to a metal oxide catalyst, comprising:

a sensor that includes:
a microheater;
a metal oxide catalyst that covers said microheater; and
a conductometric portion that is directly coupled to said microheater and includes electrodes and said metal oxide catalyst, said conductometric portion measures a conductometric response that is indicative of a change in electrical resistivity of metal oxides when exposed to said compound; and
a thermodynamic portion that includes a thermocouple and said microheater where said thermodynamic portion measures a thermodynamic response that is indicative of a heat effect associated with the catalytic decomposition of said compound, wherein said conductometric response and thermodynamic response are produced simultaneously; wherein the sensor, microheater, conductometric portion, and thermodynamic portion form a single integrated unit.

2. The gas sensor system of claim 1, wherein said compound comprises an explosive vapor.

3. The gas sensor system of claim 1 further comprising a coating that is applied over an area of said microheater to prevent said microheater from direct exposure to gas molecules.

4. The gas sensor system of claim 1, wherein said sensor comprises a thermocouple to monitor temperature activity.

5. The gas sensor system of claim 1, wherein said pre-concentrator is heated to promote thermal desorption of said compound.

6. The gas sensor system of claim 1, wherein a range of detection of said compound is in parts per billion or parts per trillion.

7. The gas sensor system of claim 1, wherein said sensor detects said compound by filtering out heat effects due to catalytic activity using said thermodynamic portion.

8. The gas sensor system of claim 7, wherein said heat effects comprises any of thermal desorption during pre-concentrator operation, sensible heat effects, adsorption heat effects to said coating, or flow rate changes.

9. The gas sensor system of claim 1 further comprising a pre-concentrator upstream from said sensor that lowers a limit of said detection of a compound.

10. The gas sensor system of claim 9, wherein said conductometric portion and said thermodynamic portion are used to minimize false positives.

11. The gas sensor system of claim 1, wherein said sensor is arranged in a MEMS device to form a sensor array for significantly reducing heat sinking to a substrate.

12. The gas sensor system of claim 11, wherein said sensor comprises a metal oxide nanowire catalyst.

13. The gas sensor system of claim 12 further comprising one or more oxide films sputtered onto said microheater-coated surface that is covered with metal oxide nanowires.

14. A method for detecting a compound using a gas sensor system, wherein the compound decomposes upon exposure to a metal oxide catalyst, said method comprising the steps of:
a. delivering said compound to a pre-concentrator for a pre-determined period of time;
b. initiating compound desorption of trapped compound by heating said pre-concentrator;
c. exposing said compound to a microheater covered by a metal oxide catalyst of a sensor;
d. measuring a conductometric response using a conductometric portion of the sensor, wherein said conductometric response is indicative of a change in electrical resistivity of metal oxide when exposed to said compound, said conductometric portion includes electrodes and said metal oxide catalyst, and is coupled to said microheater;
e. measuring a thermodynamic response using a thermodynamic portion of the sensor includes a thermocouple and said microheater, wherein said thermodynamic response is indicative of a heat effect associated with catalytic decomposition of said compound using said thermodynamic portion, said thermodynamic portion is coupled to said microheater, said conductometric response and thermodynamic response are produced simultaneously, wherein the sensor, microheater, conductometric portion, and thermodynamic portion form a single integrated unit; and
f. filtering out heat effects by said sensor to detect said compound.

15. The method of claim 14 further comprising the step of providing a thermocouple in said sensor for monitoring temperature activity.

16. The method of claim 14, wherein a range of detection of said compound is in parts per billion or parts per trillion.

17. The method of claim 14 further comprising the step of providing a coating in said sensor to prevent electrical shorts between said microheater and said catalyst.

18. The method of claim 17, wherein said heat effects comprises thermal desorption during pre-concentrator operation, adsorption heat effects to said coating, and flow rate changes.

19. The method of claim 14 further comprising the step of arranging said sensor in a MEMS device to form a sensor array for significantly reducing heat sinking to a substrate.

20. The method of claim 19, wherein said sensor comprises a metal oxide nanowire catalyst.

* * * * *